United States Patent [19]

Nagase et al.

[11] Patent Number: 5,135,005
[45] Date of Patent: Aug. 4, 1992

[54] PROCESS FOR MEASURING TEAR PRODUCTION

[75] Inventors: Makoto Nagase, Kawasaki; Kuniaki Asami, Tokyo; Motohiro Oka, Tokyo; Katsuhiko Hoshina, Tokyo, all of Japan

[73] Assignee: Showa Yakuhin Kako Co., Ltd., Japan

[21] Appl. No.: 816,100

[22] Filed: Dec. 26, 1991

Related U.S. Application Data

[60] Division of Ser. No. 620,441, Nov. 29, 1990, which is a continuation of Ser. No. 312,650, Feb. 17, 1989, abandoned.

[30] Foreign Application Priority Data

Feb. 20, 1988 [JP] Japan .................. 63-21347[U]

[51] Int. Cl.$^5$ ............................................... A61B 5/00
[52] U.S. Cl. ....................................... 128/760; 128/898
[58] Field of Search ............... 128/745, 760, 897, 898; 604/49; 33/511, 512

[56] References Cited

FOREIGN PATENT DOCUMENTS 0122032 10/1984 European Pat. Off. ............ 128/760

Primary Examiner—Randy C. Shay
Attorney, Agent, or Firm—Rosenman & Colin

[57] ABSTRACT

Disclosed is a test strip for measuring tear production. The test strip comprises a generally flat sheet material having one end rounded to be semi-circular shaped and being printed with a folding line along which said strip is bent prior to the measurement operation. The test strip is further printed with graduation marks and a scale for indicating the amount of absorbed tear. In a preferred embodiment, provided at either one or both corners of the end opposite to the rounded end is a mark indicating that the particular test strip is used for measuring one of either the left or right eye. The sheet material is preferably made of filter paper. The test strip has no notched portion which would weaken the sheet material and yet may be folded precisely along the fold line prior to use. The graduation marks and scales printed on the test strip enable easy measurement of the length of the portion wetted by tear fluid.

8 Claims, 2 Drawing Sheets

PROCESS FOR MEASURING TEAR PRODUCTION

CROSS-REFERENCE

This is a division of Ser. No. 620,441 filed Nov. 29, 1990, pending, which is a continuation of application Ser. No. 312,650 filed Feb. 17, 1989, abandoned.

BACKGROUND OF THE INVENTION

1. Field of the Invention

The present invention relates to a test strip for measuring tear production, which is used by an ophthalmologist to measure the tear production of a patient to diagnose a disease or any other abnormality of the eye.

2. Prior Art

Known test strips for measuring tear production include the Shirmer tear test strip which has a width of about 5 mm and a length of 42 mm, with its one end rounded to be semi-circular shaped, and having a triangular notch at one side of the strip spaced by about 5 mm from the rounded end. The Shirmer tear test strip is used by inserting the rounded end internally into the lower eye-lid of a patient with the rounded end bent at the notched portion, and the test result is evaluated by visually determining the length of the moistened filter paper wetted within a unit measurement of time.

However, the prior art Shirmer tear test strip has a diasadvantage in that the notched portion tends to contact the eyeball or interior surface of the lower eye-lid which causes irritation or complaint, since the strip is bent at the notched portion and then inserted internally into the lower eye-lid. The prior art Shirmer tear test strip has another disadvantage in that the moistened strip tends to break during the measurement operation since the width of the strip is narrowed by the notch. A further disadvantage of the prior art Shirmer tear test strip is confusion in determining whether a particular strip is used for the testing of the right or left eye of the patient, this being caused by difficulty in determination of obverse or reverse side of the filter paper. In addition, visual determination often leads to an inaccurate diagnosis, or a separate scale must be used for precise determination which incurs delicate operation and inconvenience in practical application.

OBJECT AND SUMMARY OF THE INVENTION

Accordingly, an object of this invention is to provide a test strip which is free from the disadvantages of the conventional Shirmer tear test strip.

A more specific object of this invention is to provide a test strip having no notched portion which would weaken the strip to often causing breakage at that portion, by being printed with a folding line along which the strip is bent or folded and further printed with graduation marks and scales for facilitating the measurement operation.

With the aforementioned object in view, the present invention provides a test strip for measuring tear production comprising a generally flat sheet material having one end rounded to be semi-circular shaped and being printed with a folding line along which said strip is bent prior to the measurement operation, said strip being further printed with graduation marks and scales for indicating the amount of absorbed tear fluid. The test strip may be ordinary paper, filter paper or nonwoven cloth, composed of a single sheet or two sheets of material, the material being substantially free of paper powder.

In a preferred embodiment, a mark is provided at either one or both corners of the end opposite to the rounded end for indicating that the particular strip is used for measuring one of either the left or right eye.

In use of the test strip of this invention, the sheet material is bent along the folding line so that the rounded end comes below the unprinted surface of the sheet material, that is, the surface printed with the graduation marks and scales is held upside down. Thereafter, the folded semi-circular end is inserted internally into the lower eye-lid and held at that position for a predetermined time period, for example 5 minutes, to allow the strip to be wetted by tear fluid. The length of the wetted portion of the test strip is measured. When the test strip is inserted into a normal or healthy eye, the length of the wetted portion of the strip ranges from 10 to 30 mm, generally about 15 mm, the length decreasing as the age of the patient increases to a considerably decreased level when the age of the patient is 60 years or more. However, it is considered that the tested eye is diseased or in abnormal condition when the length of the wetted portion of the test stip is less than 5 mm. By the use of the test strip according to this invention, the wetted length of the test strip can be readily confirmed visually by making use of the graduation marks and scales printed thereon.

DESCRIPTION OF THE DRAWINGS

In order that the invention can be more clearly understood, convenient embodiments thereof will now be described with reference to the accompanying drawings, in which.

PREFERRED EMBODIMENTS OF THE INVENTION

Preferred embodiments of the invention will now be described in detail with reference to the accompanying drawings.

Figures 1A, 1B, 1C:
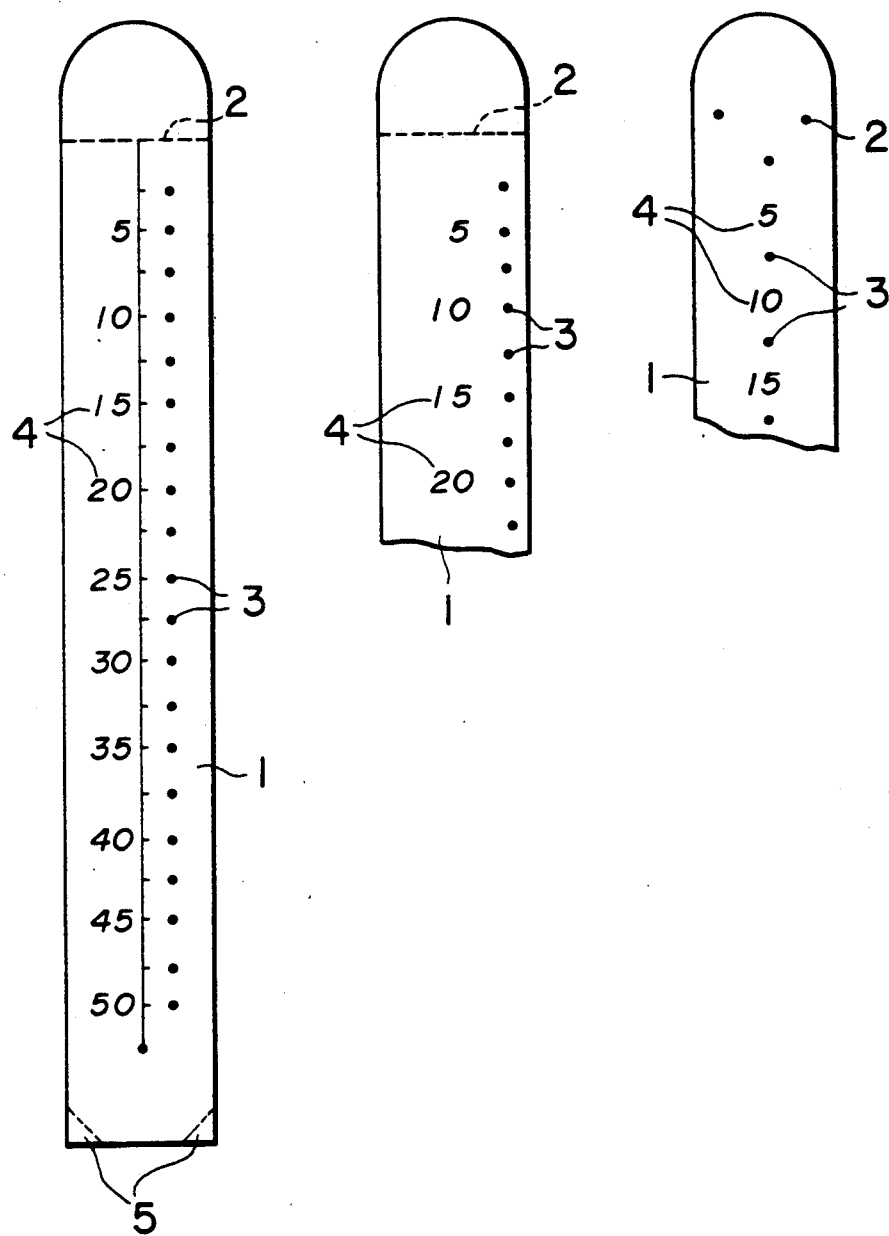
FIG. 1(A) is a plan view of one embodiment of the invention.
FIG. 1(B) is a plan view showing a portion of another embodiment of the invention.
FIG. 1(C) is a plan view showing a portion of a further embodiment of the invention.
Figure 2A:
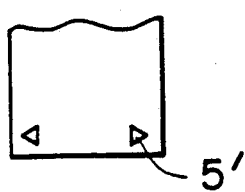
FIGS. 2(A) to 2(C) are plan views showing portions of different embodiments.
Figure 2B:
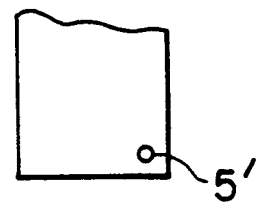
Figure 2C:
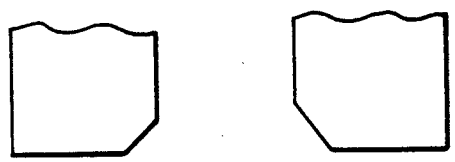

Initially referring to FIG. 1(A), a test strip 1 is made of a generally flat sheet material, for example elongated sheet-form filter paper. One end of the filter paper is rounded to be semi-circular, and a folding line 2 is marked by dots or dashes. Graduation marks 3 and scales 4 are printed while setting the folding line as the starting line. Further marks 5, which indicate that the particular test strip is used for the examination of one of either the left or right eye, are provided at the corner of the test strip opposite to the rounded end. Each of the marks 5 may be defined by a row of small perforations or roulettes, as shown in FIG. 1(A), so that it may be cut off or the area defined thereby may be shaded or hatched to indicate that the particular test strip has been used for diagnosis of the left or right eye. Otherwise, as shown in FIG. 2(A), marks 5' are printed at both corners so that either one of the marks 5' is shaded; or as shown in FIG. 2(B), either one of the corners is perforated as denoted by 5'. A futher modification is shown in FIG. 2(C) wherein one of either the left or right corner is preliminarily cut away.

Figure 3:
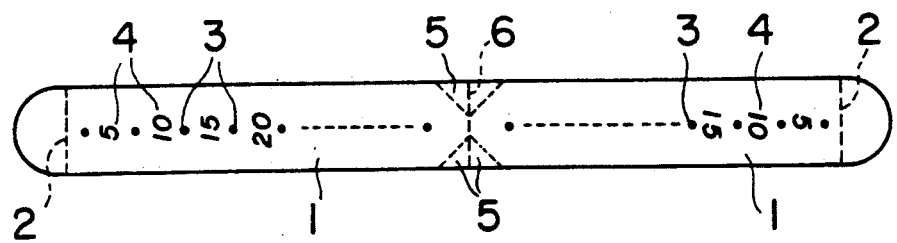
FIG. 3 is a plan view showing a still further embodiment which includes two test strips arranged in tandem fashion.

A still further embodiment of the invention is shown in FIG. 3, wherein two test strips 1, 1 are arranged in tandem fashion with their ends (the ends opposite to the rounded ends) contiguous with each other and delineated by a cutting or delineation line 6 which may be a printed line or a row of perforations or roulettes. The tandem set of test strips may be used such that one for the diagnosis of the left eye and the other for the diagnosis of the left eye. As seen by comparing FIG. 3 with FIG. 1, the graduation marks 3 and scales 4 are arranged in a somewhat different manner.

All of the marks depicted on the test strip 1, including the graduation marks 3 and scales 4, should be preferably printed by a printing ink which would not affect the wettability of the sheet material so that the amount of tear absorbed by the test strip 1 is not affected by the printing ink. Preferably, printing is effected by an ink jet printing system. Black, red, blue or other desired pigments may be used in the printing ink as long as they are not blurred by water or tear fluid. Any one or more color-developing agents or color-modifying agents may be contained in the sheet material, or may be added to the printing ink in order that the marks and scales can be clearly visual even when the sheet material is wetted by tear fluid. Examples of such agents include fluorescent materials, such as fluorescein sodium, rohdamine B and acrinol; water-soluble materials, such as FD & C Blue No. 1 which has been used as a medical coloring agent; material which are medicaments per se and used as injections or antimicrobial agents, such as phenol red and methylrosanilinium chloride; indicators used in the clinical test, such as sodium resazulin, litmus and bromthymol blue; and inorganic materials, such as cupric sulphate and cobalt chloride.

As will be apparent from the foregoing, the test strip of the invention has no notched portion which would weaken the sheet material and yet may be folded precisely along the folding line prior to use. Since the graduation marks and scales are printed while setting the folding line as the starting line or zero point, the length of the wetted portion of the test strip can be precisely determined by simple visual observation. It can be judged, without confusion, whether a particular test strip has been used for the diagnosis of left or right eye, since a mark for such purpose is provided at the end opposite to the rounded end which has been inserted into the lower eye-lid of a patient.

What is claimed is:

1. A process for measuring tear production of a patient, comprising providing a test strip of a generally flat elongated sheet material wettable by tear fluid and having a semi-circular shaped end, a longitudinally extending scale of graduation marks, and a fold line transverse to the longitudinally extending scale, folding the strip along the transverse fold line, inserting the folded strip internally into the lower eyelid of the patient, holding the test strip in place for a predetermined time period to allow the test strip to be wetted by tear fluid and measuring the length of the sheet material wetted with reference to the scale.

2. The process according to claim 1, wherein said providing step includes providing a mark indicating that the particular test strip is used for measuring one of either the left or right eye at one or both corners of the end of the strip opposite to the semi-circular shaped end.

3. The process according to claim 1, wherein said providing step includes providing a sheet material that is not susceptible to breaking or tearing even when it absorbs tear fluid and does not impair the eye when in contact with the eye.

4. The process according to claim 3, wherein said providing step includes selecting the sheet material from the group consisting of filter paper and non-woven cloth.

5. The process according to claim 1, wherein said providing step includes providing the test strip composed of a single sheet of sheet material.

6. The process according to claim 1, wherein said providing step includes providing the end opposite the semi-circular shaped end contiguous with the end opposite the semi-circular end of a second test strip.

7. The process according to claim 1, said providing step includes coloring at least one of the test strip, the graduation marks, the scale and fold line of the sheet material.

8. The process according to claim 1, wherein said providing step includes providing the test strip with marking to indicate which eye the test strip has been used for.

* * * * *